United States Patent [19]

Enlow et al.

[11] Patent Number: 5,616,767

[45] Date of Patent: Apr. 1, 1997

[54] PROCESS FOR MAKING BIPHENYLENE AND BISPHENYLENE PHOSPHITES

[75] Inventors: William P. Enlow, Belpre, Ohio; James A. Mahood, Morgantown, W. Va.

[73] Assignee: General Electric Company, Pittsfield, Mass.

[21] Appl. No.: 395,722

[22] Filed: Feb. 28, 1995

[51] Int. Cl.$^6$ .................................................. C07F 9/6574
[52] U.S. Cl. .................................................. 558/92
[58] Field of Search .................................................. 558/92

[56] References Cited

U.S. PATENT DOCUMENTS

| | | | |
|---|---|---|---|
| 4,318,845 | 3/1982 | Spivack et al. | 524/91 |
| 4,351,759 | 9/1982 | Spivack | 524/100 |
| 4,885,326 | 12/1989 | Haruna et al. | 524/291 |
| 5,137,950 | 8/1992 | Hobbs et al. | 524/120 |

FOREIGN PATENT DOCUMENTS

| | | |
|---|---|---|
| 0053098 | 6/1982 | European Pat. Off. . |
| 2087399 | 5/1982 | United Kingdom . |

OTHER PUBLICATIONS

12H–Dibenzo[d,g][1,3,2]Dioxaphosphocins: Synthesis and Evidence for Long–Range Coupling to Phosphorus; Paul A. Odorisio, Stephen D. Pastor, John D. Spivack and Leander Steinhuebel, Phosphorus and Sulfur, 1983, vol. 15, pp. 9–13 (5).

Primary Examiner—Johann Richter
Assistant Examiner—Laura L. Stockton

[57] ABSTRACT

A process is provided for making 2,2 bisphenyl phosphites and 2,2 biphenyl phosphites. The process provides pure product without requiring a recrystallization step. The process involves reacting phosphorous trichloride with either (a) an aromatic diphenol selected from the group of bisphenyl and biphenyls or (b) a monohydroxy hydrocarbon compound, to induce a first product, and then reacting the first product with the other of (a) and (b) in the presence of an amount of tri-n-alkylamine sufficient to neutralize the hydrochloric acid produced in the second reaction, and utilizing an aromatic liquid hydrocarbon medium and a minimum amount to facilitate precipitation of the resultant aromatic phosphite.

31 Claims, No Drawings

PROCESS FOR MAKING BIPHENYLENE AND BISPHENYLENE PHOSPHITES

BACKGROUND OF THE INVENTION

1. Field of the Invention

The present invention relates to a process for making biphenylene phosphites and bisphenylene phosphites, and more particularly relates to a process for making biphenylene phosphites and bisphenylene phosphites wherein solid product precipitation is formed without the need for invacuo solvent removal and residue recrystallization.

2. Description of the Related Art

Biphenytene phosphites and bisphenylene phosphites are generally known. Prior process for making such phosphites have generally involved the reaction of bisphenyl or biphenyl with phosphorous trichloride in the presence of a small amount of tri-n-alkylamine in an organic liquid medium (solvent) such as toluene. Following reaction, the resultant suspension is then filtered to remove tri-n-alkylamine hydrochloride and the liquid medium is removed invacuo. The residue is then recrystallized from an aliphatic solvent (heptane) to give fine white needs. An example of a typical prior process is set out in Paul A. Odorisio et al. "12H-Dibenzo (d,g) (1,3,2) Dioxaphosphocins: Synthesis and Evidence for Long-Range Coupling to Phosphorous" Phosphorus and Sulfur, 1983, vol. 15, pp. 9–13. Such processes undesirably require the multiple steps of filtration, vacuum removal of solvent and recrystallization of the bisphenyl/biphenyl phosphite product.

An improved process for making 3-9-diphosphaspiroundecanes was set out in Hobbs et al., U.S. Pat. No. 5,137,950, issued Aug. 11, 1992. The process involved reacting phosphorous trichloride with pentaerythritol and then reacting the product therefrom with a second hydroxyl-substituted organic compound in the presence of a tri-n-alkylamine in a molar amount equal to or greater than the molar amount of hydrogen chloride produced by the second reaction, wherein the phosphite produced is a solid product and is substantially insoluble in the medium of the second reaction. The reaction steps may be alternatively sequenced. The reference, however, neither shows nor suggests that such how to produce 2,2' biphenyl phosphide or 2,2'-bisphenyl phosphites.

Accordingly, there is a desire to provide a process to produce 2,2'-bisphenyl phosphites and/or 2,2'-bisphenyl phosphite without the need to recrystallize the product.

SUMMARY OF THE INVENTION

The present invention involves a process for making 2,2' biphenyl phosphites and 2,2' bisphenyl phosphites. The process involves reacting phosphorus trichloride with one of (a) a 2,2' biphenol or 2,2' bisphenol and (b) a second hydroxyl-substituted organic compound, and second reacting the resultant reaction product from the other of (a) and (b), the reaction being conducted in the presence of a tri-n-alkylamine wherein the tri-n-alkylamine is present in a molar amount which is equal to or greater than the molar amount of hydrogen chloride produced by the second reaction, and wherein the final product is a solid product and substantially insoluble in the medium of the second reaction. Preferably, the tri-n-alkylamine is present at a level of at least 1.5 times the molar amount of hydrogen chloride produced by the second reaction. Additionally, due to the aromatic nature of the biphenyl phosphite and the bisphenyl phosphites, it is critical to the present invention that the amount of aromatic hydrocarbon medium present during the second reaction be minimized.

DETAILED DESCRIPTION OF THE INVENTION

The 2,2 bisphenyl phosphites made pursuant to the present invention, are preferably represented by the general formula

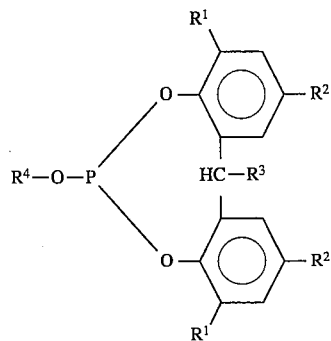

in which $R^1$ is tertiary-butyl (t-butyl) or tertiary-amyl (t-amyl), $R^2$ is an alkyl having 1 to 9 carbon atoms, $R^3$ is hydrogen or an alkyl having 1 to 4 carbon atoms, and $R^4$ is an alkyl having 1 to 30 carbon atoms or is an alkyl aryl such as 2-alkyl phenyl, 4-alkyl phenyl, 2,4-dialkyl phenyl and 2,4,6-trialkyl phenyl having from 7 to 42 carbon atoms, wherein it is preferred that the alkyl group of the alkyl aryl has from 1 to 8 carbon atoms and preferably is a t-butyl group.

Examples of suitable substituents, as the alkyl group with 1 to 9 carbon valency represented by $R^2$, methyl, ethyl, propyl, isopropyl, butyl, secondary butyl, tertiary butyl, isobutyl, amyl, tertiary amyl, hexyl, heptyl, octyl, isoctyl, 2-ethylhexyl, tertiary octyl, nonyl, tertiary nonyl and so forth. As the alkyl group with 1 to 4 carbon atomicity to be represented by $R^3$, we enumerate methyl, ethyl, propyl, isopropyl, butyl, secondary butyl, tertiary butyl, isobutyl; and as the alkyl group with 1 to 30 carbon atomicity represented by $R^4$: methyl, ethyl, propyl, isopropyl, butyl, secondary butyl, tertiary butyl, isobutyl, amyl, tertiary amyl, hexyl, heptyl, octyl, isoctyl, 2-ethylhexyl, tertiary octyl, nonyl, tertiary nonyl, decyl, isodecyl, dodecyl, tetradecyl, hexadecyl, octadecyl, eicosyl, docosyl, tetracosyl, tracontyl and so forth.

Most preferably, each $R^1$ and each $R^2$ is a t-butyl group. Most preferably, $R^3$ is a methyl group. The preferred 2,2 bisphenyl phosphite is as follows:

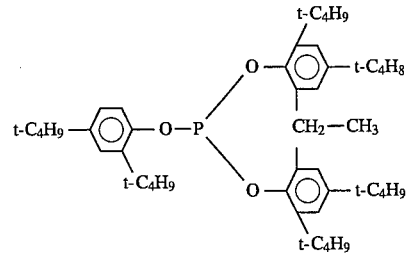

Suitable bisphenols may be represented by the general formula as follows:

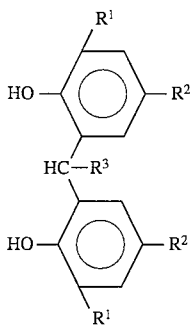

wherein each $R^1$, $R^2$ and $R^3$ is as defined above.

Suitable second hydroxyl-substituted organic compounds are represented by the general formula as follows:

$R^4$—OH wherein $R^4$ is as defined above.

Suitable biphenyl phosphites are represented by the general formula as follows:

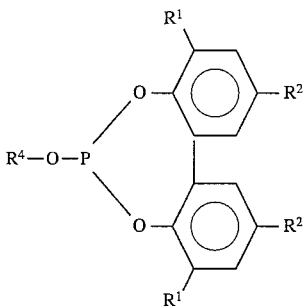

wherein $R^1$, $R^2$ and $R^4$ are as defined above.

Suitable biphenyls for making the biphenyl phosphites are as follows:

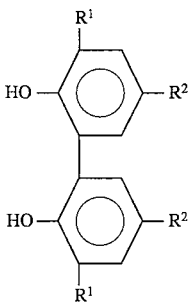

wherein $R^1$ and $R^2$ are as defined above.

The second hydroxyl-substituted organic compound suitable for making biphenyl phosphites may be the same as defined above for the bisphenyl phosphites.

It is critical to the invention that the tri-n-alkylamine be one wherein each n-alkyl moiety has at least three carbon atoms, such as n-propyl, n-butyl, n-pentyl and n-hexyl, and preferably less than 10 carbon atoms. N-butyl and n-pentyl moieties are preferred, such as in tri-n-butyl amine, tri-n-pentyl amine and di-n-butyl-n-pentylamine. Tri-n-butylamine is particularly preferred. In a preferred embodiment, the tri n-alkyl amine forms a hydrochloride salt that is substantially soluble in the reaction medium of the second reaction.

The reaction usually will be formed using one of two routes. One route involves reacting the phosphorous trichloride with bisphenyl (or biphenyl) followed by reaction of this first product with the hydroxyl-substituted organic compound in the presence of the tri-n-alkyl amine to form the desired bisphenyl (biphenyl) phosphite. Another route involves reacting the phosphorous trichloride and the second hydroxyl-substituted organic compound, followed by reacting the first product with the bisphenyl (bisphenyl) in the presence of the tri-n-alkylamine to form the desired bisphenyl phosphite (biphenyl phosphite). The tri-n-alkylamine is to be present in an amount which is at least sufficient to substantially neutralize the acid formed during the formation of the final phosphite product, and most preferably this will be a molar amount of at least 1.5 times the molar amount of bisphenyl (biphenyl) reacted in the reaction process.

Consistent with the invention, the hydroxyl-substituted organic compound may be any of a variety of hydroxyl-substituted organic compounds, including alkanols, phenols, and hydroxyl-substituted cycloalkanes, and hydroxyl-substituted aralkyls, such as octadecanol, alkylated phenols, cyclohexanol and phenylethanol. The phenol preferably is selected from the group consisting of 2,4,6-tri-alkyl phenols and 2,4-di-alkyl phenols, such as 2,4,6-tri-alkyl phenols and 2,4-di-alkyl phenols, such as 2,4,6-tri-t-butyl phenol, 2,4-di-t-butyl phenol, 2,4,6-tri-t-pentylphenol, 2,6-di-t-butyl-4-sec-butylphenol, 2,4-di-t-butylphenol, and 2-t-butyl-4-methylphenol. However, 2,4-di-t-alkyl phenols such as 2,4-di-t-butylphenol, and 2,6-di-t-alkyl-4-alkyl phenols, such as 2,4,6-tri-t-butylphenol, 2,6-di-t-butyl-4-methyl phenol, 2,6-di-t-butyl-4-ethyl phenol, 2,4-di-t-butylphenol, and 2,6-di-t-butyl-4-t-butyl phenol are preferred. The 2,4,6-tri-t-alkyl phenols, 2,6-di-t-alkyl-4-n-alkyl phenols, 2,6-di-t-alkyl-4-n-alkyl phenols and 2,4-di-t-alkyl phenols are most preferred.

If the present process is involved with the first route set out above, then preferably phosphorous trichloride utilized in the first reaction step is present in the molar ratio of between 1:1 and 3:1 relative to the bisphenyl (biphenyl) molar amount. The product obtained therefrom (the first product) is preferably reacted with the second hydroxyl-substituted organic compound in a molar ratio of between 1 and 1.2:1.

If the second route set out above is utilized, then preferably the first reaction utilized the phosphorous trichloride in a molar ratio to the second hydroxyl-substituted organic compound of between 1:1 and 4.5:1. The first product from this second route is then preferably reacted with the bisphenyl (biphenyl) in a molar ratio of between 1 and 1.1:1.

A critical feature of the present invention is to minimize the amount of organic liquid medium (solvent) utilized in the reaction process. The amount of medium is less than 3:1 based on the total final weight of bisphenyl phosphite (biphenyl phosphite) produced. The low level of organic medium facilitates precipitation of the phosphite product.

The phosphites made by the process of the present invention maybe used in an effective amount in polymer compositions for stabilization thereof. An amount of the phosphites of the invention is considered to be an "effective amount" when the polymer composition containing the phosphites of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more. The polymer composition may be thermoset in nature including unsaturated polyesters, phenolics, epoxie, urethanes, coating resins and crosslinkable latexes.

The polymer may also be any thermoplastic known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinyl chloride/ABS or other impact modified polymers, such as methacrylonitrile and alphamethylstyrene containing ABS, and polyester/ABS or polycarbonate/ABS and polyester plus some other impact modifier may also be used. Such polymers are available commercially or may be made by means well known in the art. However, the phosphites of the invention are particularly useful in thermoplastic polymers, such as polyolefins, polycarbonates, polyesters, polyphenylene ethers and styrenic polymers, due to the extreme temperatures at which thermoplastic polymers are often processed and/or used. Recycled thermoplastics may also be used.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidenenorbornene; as well as mixtures of such copolymers and their mixtures with polymers mentioned above, for example polypropylene/ethylene propylene-copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene styrene. Styrenic polymers may additionally or alternatively include graft copolymers of styrene or alpha-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; sytrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/-butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo- and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally platicized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2(2,2,4(4-hydroxyphenyl)-propane) terephthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred. Also included are biodegradable polymers such as polylactide and starch modified polymers.

The resulting stabilized polymer compositions of the invention may optionally also contain various conventional additives, such as the following:

1. Antioxidants 1.1 Alkylated monophenols, for example: 2,6-di-tertbutyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(alpha-methylcyclohexyl)-4,6 dimethylphenol, 2,6-di-octadecyl-4-methylphenol, 2,4,6,-tricyclohexyphenol, 2,6-di-tert-butyl-4-methoxymethylphenol.

1.2 Alkylated hydroquinones, for example, 2,6-di-tert-butyl-4-methoxyphenol, 2,5-di-tert-butyl-hydroquinone, 2,5-di-tert-amyl-hydroquinone, 2,6-diphenyl-4octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl-3-methylphenol), 4,4'-thio-bis-(6-tert-butyl-2-methylphenol).

1.4 Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(alpha-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(alpha-methylbenzyl)-4-nonylphenol), 2,2'-methylene-bis-(6-(alpha, alpha-dimethylbenzyl)-4-nonyl-phenol). 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis(5-tert-butyl-4-hydroxy-2-methylphenol)butane. 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy 2-methylphenyl)-3-dodecyl-mercaptobutane, ethyleneglycol-bis-( 3,3,-bis-(3'-tert-butyl-4'-hydroxyphenyl)-butyrate)-di-(3-tert-butyl-4-hydroxy-5-methylphenyl)-dicyclopentadiene, di-(2-(3'-tert-butyl-2'hydroxy-5'-methyl-benzyl)-6-tert-butyl-4-methylphenyl) terephthalate.

1.5 Benzyl compounds, for example, 1,3,5-tris(3,5-di-tert-butyl-4-hydroxybenzyl)-2,4,6-trimethylbenzene, bis-(3, 5-di-tert-butyl-4hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate. 1,3,5-tris-(3,5-di-tert-butyl-4-hydroxybenzyl)isocyanurate. 1,3,5-tris-(4-tert-butyl-3-hydroxy-2,6-dimethylbenzyl)isocyanurate, dioctadecyl 3,5-di-tert-butyl-4-hydroxybenzyl-phosphonate, calcium salt of monoethyl 3,5-di-tert-butyl-4-hydroxybenzyl-phosphonate, 1,3,5-tris-(3,5-dicyclohexyl-4-hydroxybenzyl)isocyanurate.

1.6 Acylaminophenols, for example, 4-hydroxy-lauric acid anilide, 4-hydroxy-stearic acid amilide, 2,4-bis-octylmercapto-6-(3, 5-tert-butyl-4-hydroxyanilino)-s-triazine, octyl-N-(3,5-di-tert-butyl-4-hydroxyphenyl)-carbamate.

1.7 Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, penta-erythritol, neopentylglycol, tris-hydroxyethyl isocyanurate, thiodiethyleneglycol, di-hydroxyethyl oxalic acid diamide.

1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy-3-methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4-hydroxyphenol)-propionic acid for example, N,N'-di-(3,5-di-tert-butyl-4-hydroxyphenylpropionyl)-hexamethylen-diamine, N,N'-di-(3, 5-di-tert-butyl-4-hydroxyphenylpropionyl)trimethylenediamine, N,N'-di-(3, 5-di-tert-butyl-4-hydroxyphenylpropionyl)hydrazine.

2. UV absorbers and light stabilizers.

2.1 2-(2'-hydroxyphenyl)-benzotriazoles, for example, the 5'methyl-,3'5'-di-tert-butyl-, 5'-tert-butyl-,5'(1,1,3,3-tetramethylbutyl)-,5-chloro-3',5'-di-tert-butyl-,5-chloro-3'tert-butyl-5'methyl-, 3'sec-butyl-5'tert-butyl-, 4'-octoxy, 3',5'-ditertamyl-3',5'-bis-(alpha, alpha-dimethylbenzyl)-derivatives.

2.2 2-Hydroxy-benzophenones, for example, the 4-hydroxy-4-methoxy-,4-octoxy,4-decyloxy-, 4-dodecyloxy-,4-benzyloxy,4,2',4'-trihydroxy-and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butylphenyl-3,5-di-tert-butyl-4-hydroxybenzoate and hexadecyl-3,5-di-tert-butyl-4-hydroxybenzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

2.5 Nickel compounds, for example, nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

2.6 Sterically hindered amines, for example bis(2,2,6,6-tetramethylpiperidyl)-sebacate, bis-(1,2,2,6,6-pentamethlpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl) sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperdine; and N-(1-hydroxy-2,2,6,6-tetramethyl-piperidin-4-yl)-epsiloncaprolactam.

2.7 Oxalic acid diamides, for examples, 4,4'-dioctyloxy-oxanilide, 2,2'-di-octyloxy-5',5'-di-tert-butyloxanilide, 2,2'-di-dodecyloxy-5',5'di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of ortho-and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, and tetrakis(2,4-di-tert-butylphenyl) 4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmitate, antimony pyrocatecholate or zinc pyrocatecholate.

8. Nucleating agents, for example, salts of benzoic acid, 4-tert butylbenzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N,N-dibenzylaminoxy)propanoate;ethyl-3-(N,N-dibenzylaminoxy)propanonoate; 1,6-hexamethylene-bis(3-N, N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

11. Other additives, for example, plasticizers, lubricants, emulsifiers, pigments, optical brighteners, flameproofing agents, anti-static agents, blowing agents and thiosynergists such as dilaurythiodipropionate or distearylthiodipropionate.

Polymeric particles may be coated with the present phosphites alone or in combination with other stabilizers for stabilization of the polymeric material. Particles may be spherical in shape and may be made by processes such as "Reactor Granule Technology" as disclosed in P. Galli and J. C. Halock, The Reactor Granule—A Unique Technology for the Production of a New Generation of Polymer Blends, Society of Plastics Engineers, Polyolefin III International Conference Feb. 24–27, 1991 and as disclosed in Pedrazzeth et al. U.S. Pat. No. 4,708,979 entitled Process for the Stabilization of Spherically Polymerized Polyolefins issued Nov. 24, 1987 both of which are disclosed herein by reference. Particle formation may be achieved by supported Ziegler-Natta Catalyst systems. Suitable commercial processes are known by the trademarks: Spheripol, Addipol and Spherilene.

Olefin polymers may be produced by polymerization of olefins in the presence of Ziegler-Natta catalysts optionally on supports such as but not limited to Mg $Cl_2$, chromium salts and complexes thereof, optionally supported on Silica or other materials. They may also be produced utilizing catalysts based on cyclopentadiene complexes of metals typically complexes of Ti or Zr.

Consistent with the invention, the phosphites of the invention may be added to the polymer at any time prior to or during fabrication into articles and may be combined with the polymer by any of a variety of means known in the art, such as by preblending or by being fed directly into fabrication equipment.

The polypropylene compositions may include residual catalyst such as Ziegler catalysts which may be carried on a support (i.e. $TiCl_3$ on $MgCl_2$). Other stabilizers may also be incorporated in the compositions.

The liquid organic medium used for the present process is an aromatic organic compound, preferably selected from the group consisting of toluene and chlorobenzene. Due to the aromatic nature of the phosphite, and the aromatic nature of the liquid medium, it is critical in the process of the present invention to minimize the amount of liquid medium present in order to maximize the precipitation of the final product.

EXAMPLES

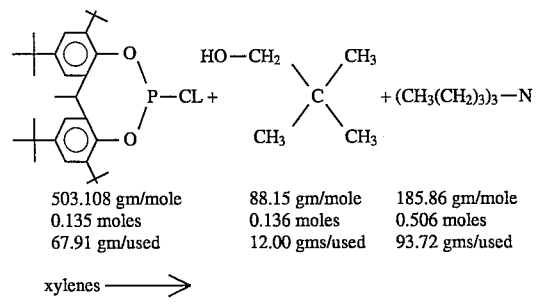

| 503.108 gm/mole | 88.15 gm/mole | 185.86 gm/mole |
| 0.135 moles | 0.136 moles | 0.506 moles |
| 67.91 gm/used | 12.00 gms/used | 93.72 gms/used | xylenes ⟶

-continued

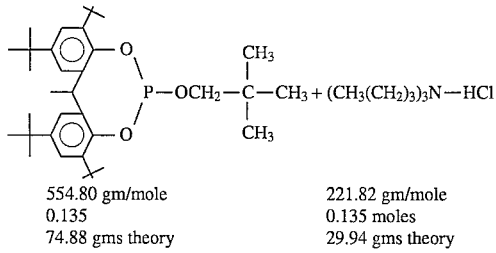

| 554.80 gm/mole | 221.82 gm/mole |
| 0.135 | 0.135 moles |
| 74.88 gms theory | 29.94 gms theory |

Into a 1 liter 3-necked flask was weighed 67.91 grams of 2,2'ethylidine bis(4,6-di-t-butyl-phenyl) chlorophosphite. 93.71 grams of tri-n-butylamine was added. The reaction flask was equipped with a stir shaft and paddle, a thermometer and condenser. The mixture was immediately placed under a nitrogen blanket. The mixture was heated to 75° C. in an attempt to dissolve the chlorophosphite. The solids did not totally dissolve. 25.0 grams of xylene was added to the mixture. The mixture has almost totally dissolve 12.00 grams of neopentyl alcohol was melted and added to the reaction mixture. The materials in the flask immediately turned white and colidified. An additional 70 mol of tri-n-butylamine was added to slurry the mixture. The mixture was stirred until a homogenous slurry was obtained. The mixture was heated to 102° C. and the heating mantle was removed. The mixture was allowed to cool to 35° C.

300 ml of of isopropyl alcohol was added to the reaction mixture and stirred for 20 minutes. The white solids were isolated by filtration through a 600 micron fitted disc filtering funnel. The white solids were sucked to dryness on the filter. The solids were returned to the reaction flask and reslurried in 300 mol of isopropyl alcohol, stirred for 10 minutes and isolated by filtration. The white solids were sucked to dryness on the filter by use of a rubber dam. The white solids were reslurried a third time in isopropyl alcohol and isolated by filtration. The material was sucked to dryness by use of a rubber dam then dried under a 1 torr vacuum at room temperature for a period of 30 minutes. The vacuum was broken and the material placed under nitrogen.

The white solids were dried on the rotary flask evaporator to 88° C. at 1 torr. The white solids were analyzed by liquid chromotography.

A melt point was obtained on the material. The white solid melted at 258°–259° C.

An acid number determination was performed using the methylene chloride procedure. The acid value is 0.197 mg KOA/grams of sample 62.81 grams of material was obtained using this technique. This results in a yield of 83.88%.

What is claimed is:

1. A process for making a phosphite compound, said phosphite compound being a biphenylene phosphite compound or a bisphenylene phosphite compound, said process comprising:
   (a) reacting phosphorus trichloride with a first hydroxyl-substituted compound selected from one of either:
      (a)(i) a hydroxyl-substituted compound selected from 2,2'-bisphenol compounds and 2,2'-biphenol compounds, or
      (a)(ii) a hydroxyl-substituted compound selected from phenol, alkanols, hydroxyl-substituted cycloalkanes and hydroxyl-substituted aralkyl compounds to form a reaction intermediate;
   (b) reacting the reaction intermediate with a second hydroxyl-substituted compound of (a)(i) or (a)(ii) that is other than the first hydroxyl-substituted compound selected in step (a) to form the phosphite compound, wherein:
      the reaction of step (b) produces hydrogen chloride,
      the reaction of step (b) is conducted in an amount of an aromatic hydrocarbon medium that is less than 25 percent by weight of the amount of phosphite compound produced in the reaction of step (b),
      the reaction of step (b) is conducted in the presence of a molar amount of a tri n-alkyl amine, each of the n-alkyl moieties of the amine having a least three carbon atoms per moiety, that is equal to or greater than the molar amount of hydrogen chloride that is produced during the reaction of step (b), and
      the phosphite compound is insoluble in the aromatic hydrocarbon medium;
   (c) isolating the phosphite compound from the aromatic hydrocarbon medium; and
   (d) purifying the phosphite compound without recrystallizing the phosphite compound.

2. The process of claim 1, wherein the amine forms a hydrochloride salt that is substantially soluble in said aromatic hydrocarbon medium.

3. The process of claim 1, wherein the phosphite compound is purified by washing the phosphite compound with isopropanol.

4. The process of claim 1, wherein the first hydroxyl-substituted compound is a 2,2'-biphenol compound and the phosphite compound is a 2,2'-biphenylene phosphite compound.

5. The process of claim 1, wherein the first hydroxyl-substituted compound is a 2,2'-bisphenol compound and the phosphite compound is a 2,2'-bisphenylene phosphite compound.

6. The process of claim 1, wherein the first hydroxyl-substituted compound is a compound having a structural formula according to:

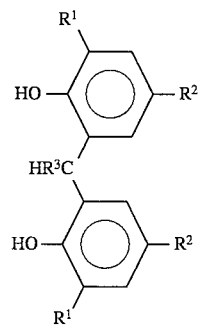

or

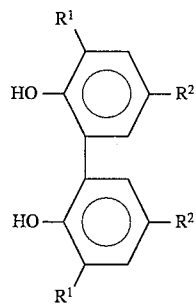

wherein:

$R^1$ is tertiary-butyl or tertiary-amyl, $R^2$ is an alkyl having 1 to 9 carbon atoms, and $R^3$ is a hydrogen or an alkyl having 1 to 4 carbon atoms.

7. The process of claim 1, wherein the second hydroxyl-substituted compound is a 2,4-dialkyl phenol or a 2,4,6-trialkyl phenol.

8. The process of claim 1, wherein the n-alkyl moieties of the tri-n-alkyl amine each include from 3 to 10 carbon atoms per moiety.

9. The process of claim 8, wherein the n-alkyl moieties of the tri-n-alkyl amine are each n-propyl, n-butyl, n-pentyl or n-hexyl.

10. The process of claim 1, wherein the tri-n-alkyl amine is tri-n-butyl amine.

11. The process of claim 1, wherein phosphorus trichloride and the first hydroxyl-substituted compound are reacted in step (a) and wherein the intermediate and the second hydroxyl-substituted compound are reacted in step (b).

12. The process of claim 11, wherein phosphorus trichloride and the first hydroxyl-substituted compound are used in a ratio of from 1 to 3 moles of phosphorus trichloride per 1 mole of the first hydroxyl-substituted compound.

13. The process of claim 11, wherein the intermediate and the second hydroxyl-substituted compound are used in a ratio of from 1 to 1.2 moles of the intermediate per mole of the second hydroxyl-substituted compound.

14. The process of claim 1, wherein phosphorus trichloride and the second hydroxyl-substituted compound are reacted in step (a) and wherein the intermediate and the first hydroxyl-substituted compound are reacted in step (b).

15. The process of claim 14, wherein phosphorus trichloride and the second hydroxyl-substituted compound are used in a ratio of from 1 to 4.5 moles of phosphorus trichloride per 1 mole of the second hydroxyl-substituted compound.

16. The process of claim 14, wherein the intermediate and the first hydroxl-substituted compound are used in a ratio of from 1 to 1.2 moles of the intermediate per 1 mole of the first hydroxyl-substituted compound.

17. A process for making a phosphite compound, said phosphite compound being a biphenylene phosphite compound or a bisphenylene phosphite compound, said process comprising:

(a) reacting phosphorus trichloride with a first hydroxyl-substituted compound selected from one of either:

(a)(i) a hydroxyl-substituted compound selected from 2,2'-bisphenol compounds and 2,2'-biphenol compounds, or (a)(ii) a hydroxyl-substituted compound selected from phenol, alkanols, hydroxyl-substituted cycloalkanes and hydroxyl-substituted aralkyl compounds to form a reaction intermediate;

(b) reacting the reaction intermediate with a second hydroxyl-substituted compound of (a)(i) or (a)(ii) that is other than the first hydroxyl-substituted compound selected in step (a) to form the phosphite compound, wherein:

the reaction of step (b) produces hydrogen chloride, the reaction of step (b) is conducted in an amount of an aromatic hydrocarbon medium that is less than 25 percent by weight of the amount of phosphite compound produced in the reaction of step (b), the reaction of step (b) is conducted in the presence of a molar amount of a tri n-alkyl amine, each of the n-alkyl moieties of the amine having a least three carbon atoms per moiety, that is equal to or greater than the molar amount of hydrogen chloride that is produced during the reaction of step (b), the amine forms a hydrochloride salt that is substantially soluble in said aromatic hydrocarbon medium, and the phosphite compound is insoluble in the aromatic hydrocarbon medium;

(c) isolating the phosphite compound from the aromatic hydrocarbon medium; and (d) purifying the phosphite compound without recrystallizing the phosphite compound.

18. The process of claim 17, wherein the phosphite compound is purified by washing the phosphite compound with isopropanol.

19. The process of claim 17, wherein the first hydroxyl-substituted compound is a 2,2'-biphenol compound and the phosphite compound is a 2,2'-biphenylene phosphite compound.

20. The process of claim 17, wherein the first hydroxyl-substituted compound is a 2,2'-bisphenol compound and the phosphite compound is a 2,2'-bisphenylene phosphite compound.

21. The process of claim 17, wherein the first hydroxyl-substituted compound is a compound having a structural formula according to:

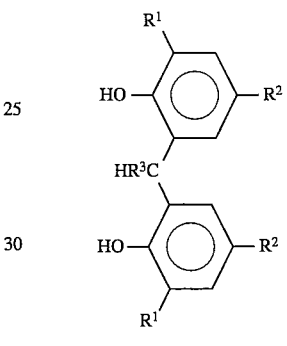

or

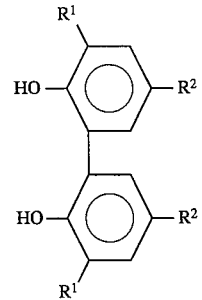

wherein:

$R^1$ is tertiary-butyl or tertiary-amyl, $R^2$ is an alkyl having 1 to 9 carbon atoms, and $R^3$ is a hydrogen or an alkyl having 1 to 4 carbon atoms.

22. The process of claim 17, wherein the second hydroxyl-substituted compound is a 2,4-dialkyl phenol or a 2,4,6-trialkyl phenol.

23. The process of claim 17, wherein the n-alkyl moieties of the tri-n-alkyl amine each include from 3 to 10 carbon atoms per moiety.

24. The process of claim 23, wherein the n-alkyl moieties of the tri-n-alkyl amine are each n-propyl, n-butyl, n-pentyl or n-hexyl.

25. The process of claim 17, wherein the tri-n-alkyl amine is tri-n-butyl amine.

26. The process of claim 17, wherein phosphorus trichloride and the first hydroxyl-substituted compound are reacted in step (a) and wherein the intermediate and the second hydroxyl-substituted compound are reacted in step (b).

27. The process of claim 26, wherein phosphorus trichloride and the first hydroxyl-substituted compound are used in a ratio of from 1 to 3 moles of phosphorus trichloride per 1 mole of the first hydroxyl-substituted compound.

28. The process of claim 26, wherein the intermediate and the second hydroxyl-substituted compound are used in a ratio of from 1 to 1.2 moles of the intermediate per mole of the second hydroxyl-substituted compound.

29. The process of claim 17, wherein phosphorus trichloride and the second hydroxyl-substituted compound are reacted in step (a) and wherein the intermediate and the first hydroxyl-substituted compound are reacted in step (b).

30. The process of claim 29, wherein phosphorus trichloride and the second hydroxyl-substituted compound are used in a ratio of from 1 to 4.5 moles of phosphorus trichloride per 1 mole of the second hydroxyl-substituted compound.

31. The process of claim 29, wherein the intermediate and the first hydroxl-substituted compound are used in a ratio of from 1 to 1.2 moles of the intermediate per 1 mole of the first hydroxyl-substituted compound.

* * * * *